United States Patent
Goetz

(10) Patent No.: US 7,614,099 B2
(45) Date of Patent: Nov. 10, 2009

(54) VIBRATABLE, SOUND-EMITTING, AND INFLATABLE SLEEPING BAG FOR PROVIDING DEEP PRESSURE

(76) Inventor: Anne Goetz, 6 Pitching Way, Scotch Plains, NJ (US) 07076

( * ) Notice: Subject to any disclaimer, the term of this patent is extended or adjusted under 35 U.S.C. 154(b) by 218 days.

(21) Appl. No.: 11/449,356

(22) Filed: Jun. 7, 2006

(65) Prior Publication Data
US 2006/0277680 A1    Dec. 14, 2006

Related U.S. Application Data

(60) Provisional application No. 60/688,606, filed on Jun. 8, 2005.

(51) Int. Cl.
*A47G 9/08* (2006.01)
*A47C 27/10* (2006.01)
*A61H 1/00* (2006.01)

(52) U.S. Cl. .................. 5/413 R; 5/413 AM; 601/49; 601/57

(58) Field of Classification Search ............ 5/413 R, 5/413 AM, 904, 915, 639, 644, 654, 655.3, 5/706, 710, 713; 2/69, 69.5; 601/46, 47, 601/49, 56–59
See application file for complete search history.

(56) References Cited

U.S. PATENT DOCUMENTS

| 867,464 | A | * | 10/1907 | Abbott | 5/413 R |
|---|---|---|---|---|---|
| 1,324,009 | A | * | 12/1919 | Hope | 5/413 R |
| 1,608,239 | A | * | 11/1926 | Rosett | 601/152 |
| 1,648,373 | A | * | 11/1927 | Vilas | 5/413 R |
| 2,361,242 | A | * | 10/1944 | Rosett | 601/152 |
| 3,450,450 | A | * | 6/1969 | Hopkins et al. | 312/1 |
| 3,751,741 | A | * | 8/1973 | Hendry | 5/413 AM |
| 3,798,686 | A | * | 3/1974 | Gaiser | 5/413 AM |
| 3,877,092 | A | * | 4/1975 | Gaiser | 5/413 R |
| 4,091,482 | A |   | 5/1978 | Malcolm |  |
| 4,092,750 | A | * | 6/1978 | Ellis | 5/413 AM |
| 4,157,088 | A | * | 6/1979 | Gracey | 601/57 |
| 4,192,030 | A | * | 3/1980 | Casson | 5/420 |
| 4,355,632 | A | * | 10/1982 | Sandman | 601/152 |
| 4,641,386 | A |   | 2/1987 | Heinz et al. |  |
| 4,862,533 | A | * | 9/1989 | Adams, III | 5/413 R |

(Continued)

FOREIGN PATENT DOCUMENTS

GB      2170100 A * 7/1986

OTHER PUBLICATIONS

Southpaw Enterprises, http://www.southpawenterprises.com, Product Name: Weighted Blanket Animals—Ladybug, Date of Access: May 25, 2006.

(Continued)

*Primary Examiner*—Robert G Santos
(74) *Attorney, Agent, or Firm*—Lowenstein Sandler PC

(57) ABSTRACT

A vibratable and sound emitting sleeping bag with an inflatable interior lining that may be inflated by the bag's occupant to provide deep pressure to the bag occupant's body when enclosed in the bag. The level of pressure applied to the individual is adjustable by a pump, adapted for control by a small child. The sleeping bag vibrates and produces sound to provide the bag's occupant with additional sensory stimulation. The sleeping bag is particularly suited for use by an autistic child for reducing the effects of autism-related anxiety and discomfort.

13 Claims, 1 Drawing Sheet

U.S. PATENT DOCUMENTS

| | | | | |
|---|---|---|---|---|
| 4,872,229 | A * | 10/1989 | Brady | 5/710 |
| 4,896,387 | A | 1/1990 | Malcolm et al. | |
| 4,941,453 | A * | 7/1990 | Shakas et al. | 600/28 |
| 4,947,832 | A | 8/1990 | Blitzer | |
| 4,991,222 | A * | 2/1991 | Nixdorf | 381/388 |
| 4,996,733 | A * | 3/1991 | Tsai | 5/413 R |
| 5,005,236 | A * | 4/1991 | Hutchinson | 5/413 AM |
| 5,014,687 | A * | 5/1991 | Raffel | 601/59 |
| 5,140,977 | A * | 8/1992 | Raffel | 601/46 |
| 5,392,477 | A | 2/1995 | Wolter et al. | |
| 5,471,687 | A * | 12/1995 | Vierra | 5/413 AM |
| 5,528,779 | A * | 6/1996 | Lee et al. | 5/413 AM |
| 5,553,339 | A * | 9/1996 | Thomas | 5/413 AM |
| 5,560,056 | A * | 10/1996 | Tai | 5/120 |
| 5,640,725 | A * | 6/1997 | Ando et al. | 5/413 AM |
| 5,669,088 | A | 9/1997 | McNamee | |
| 5,740,565 | A | 4/1998 | McDade | |
| 5,938,628 | A * | 8/1999 | Oguri et al. | 601/150 |
| 6,170,602 | B1 | 1/2001 | Mann | |
| 6,321,400 | B1 * | 11/2001 | Gulino | 5/413 AM |
| 6,675,414 | B2 * | 1/2004 | Lamke | 5/413 AM |
| 6,799,339 | B2 * | 10/2004 | Stewart | 5/413 AM |
| 6,990,696 | B2 * | 1/2006 | Stewart et al. | 5/413 R |
| 7,051,386 | B2 * | 5/2006 | Stewart et al. | 5/413 R |
| 7,418,748 | B2 * | 9/2008 | Lamke | 5/413 AM |
| 2001/0054192 | A1 | 12/2001 | Haar et al. | |
| 2002/0104162 | A1 * | 8/2002 | Stewart | 5/413 AM |
| 2002/0188999 | A1 | 12/2002 | Haar et al. | |
| 2003/0074711 | A1 * | 4/2003 | Iversen | 2/69 |
| 2004/0216238 | A1 * | 11/2004 | Stewart et al. | 5/722 |
| 2005/0034235 | A1 | 2/2005 | Bellick et al. | |
| 2005/0060803 | A1 * | 3/2005 | Stewart et al. | 5/413 AM |
| 2006/0277680 | A1 * | 12/2006 | Goetz | 5/413 AM |
| 2007/0074348 | A1 * | 4/2007 | Carlton | 5/639 |

OTHER PUBLICATIONS

Southpaw Enterprises, http://www.southpawenterprises.com, Product Name: Bear Hug; Date of Access: May 25, 2006.

Southpaw Enterprises, http://www.southpawenterprises.com, Product Name: Bear Hug Weighted Wrap, Date of Access: May 25, 2006.

Southpaw Enterprises, http://www.southpawenterprises.com, Product Name: Dolphin Wrap, Date of Access: May 25, 2006.

Southpaw Enterprises, http://www.southpawenterprises.com, Product Name: Flannel Weighted Shawl Unsented, Date of Access: May 25, 2006.

Southpaw Enterprises, http://www.southpawenterprises.com, Product Name: Weighted Blanket, Date of Access: May 25, 2006.

* cited by examiner

VIBRATABLE, SOUND-EMITTING, AND INFLATABLE SLEEPING BAG FOR PROVIDING DEEP PRESSURE

CROSS-REFERENCE TO RELATED APPLICATION

This application claims the benefit of U.S. Provisional Application No. 60/688,606, filed Jun. 8, 2005. U.S. Provisional Application No. 60/688,606 is hereby incorporated herein by reference.

FIELD OF THE INVENTION

The present invention relates generally to a sleeping bag having an inflatable interior section, and, more specifically, to a sleeping bag that provides adjustable levels of deep pressure to surround the bag's occupant via one or more inflatable bladders controllably via a pump attachment. The sleeping bag is particularly suited for use by an autistic person.

BACKGROUND OF THE INVENTION

Autism is a neurodevelopment disorder that manifests itself in markedly abnormal social interaction, communication ability, patterns of interests, and patterns of behavior.

Although the specific etiology of autism is unknown, many researchers suspect that autism results from genetically mediated vulnerabilities to environmental triggers, and is generally evident in children by the age of three. It is estimated that, in the United States, autism occurs in as many as 1 in 166 children.

Some children with autism have improved their social and other skills to the point that they can fully participate in mainstream education and social events, but there are no indications that a cure for autism is possible with current technology or advances in medicine.

There is a great diversity in the skills and behaviors of individuals diagnosed as autistic. Much of this is due to the sensory system of autistics, which is quite different from the sensory system of other people, since certain stimulations can affect an autistic person differently from how they would a non-autistic person, and the degree to which the sensory system is affected varies considerably from one autistic person to another.

A key characteristic of children with autism is that they display symptoms much like those found in sensory integration dysfunction. These children exhibit problems coping with the normal sensory input. Indicators of this disorder include oversensitivity or under reactivity to touch, movement, sights, or sounds; poor body awareness; difficulty learning new motor skills or movements; and social and/or emotional problems.

Sensory experiences involve touch, movement, body awareness, sight, sound, and the effects of gravity on the body. The process wherein the brain organizes and interprets all of this sensory information at the same time is generally referred to as "sensory integration." Some disabilities, such as autism, make it difficult to organize sensory input and interpret environmental stimuli and can lead to stress and anxiety.

It has been found that certain kinds of sensory stimulation can help the neurological system to normalize and adjust the accuracy of the body's sensory perception. For example, a tactile stimulation can affect tactile perception, body awareness, motor planning, visual perception, and learning capability. Additionally, tactile and auditory stimulation have been shown to decrease autistic children's feelings of anxiety and discomfort.

Research has found that the application of deep touch stimulation, referred to as "deep pressure," helps to produce a calming effect on hyperactive and autistic individuals. Deep pressure is used to reduce anxiety's debilitating effects. Generally speaking, deep touch pressure is the type of surface pressure that is exerted in most types of firm touching, holding, hugging, or other physical contact. To soothe the effects of anxiety, the pressure is typically "deep," often intense pressure. However, achieving the appropriate level or amount of pressure may be problematic. The term "deep pressure" as it is used herein refers to, but is not limited to, the level of pressure necessary to produce a calming affect. The level of pressure necessary to achieve a calming effect will differ from one person to another and from one location on the body to another.

One method that has been used comfort autistic children is to provide deep pressure massages or hugs. Another method is to create what is known as a "kid burrito" by rolling the child up tightly in a blanket, or what is known as a "kid sandwich" by squeezing the child between two gymnastic mats or sofa cushions. These methods, however, present practical problems. Specifically, it is difficult for a parent—or other person with whom the child is comfortable—to be consistently available to provide the therapy. This is especially the case in view of the vicissitudes of the needs of an autistic child. Additionally, these methods do not allow specificity with regard to the particular parts of the body upon which the child desires the pressure and the particular level of pressure desired. Finally, these methods can only be applied in limited environments, as they might subject the child to social discomfort if performed in public.

A conventional apparatus for providing deep pressure is known as the "Hug Box," developed by Temple Grandin. The Hug Box is made of two padded side-boards which are hinged near the bottom to form a V-shape. In operation, a user lies down or squats inside the V-shaped opening of the apparatus, and, by using a lever, engages an air cylinder, which pushes the side-boards together. The side-boards make contact with the subject and provide deep pressure stimulation evenly across the lateral parts of the body. However, this apparatus is large and not portable. Furthermore, due to its size, the apparatus may not be safe for use by children.

Other conventional methods of providing deep pressure include the use of weighted materials to cover or be worn by the individual. Examples of these weighted devices include weighted vests, weighted blankets, and weighted bands, all of which are designed to provide the individual with a source of deep pressure. However, the use of weighted materials is limited to a static amount of pressure, i.e., the weighted materials provide an amount of pressure applied that may not be adjusted to suit the needs of the user. The weighted coverings provide a static level of pressure, which over time, tends to numb the individual, thereby reducing the therapeutic benefits of the deep pressure. These products offer only a single level of pressure to the user that can not be adjusted according to the individual's needs or desires.

Another effective deep touch stimulation treatment technique is rhythmic vestibular stimulation. For example, the use of vibration provides input to the body and the brain, and helps stimulate body awareness and motor function accuracy, facilitating a feeling of calmness.

Yet another technique for assisting sensory integration involves the use of auditory input stimulation of a calming nature, such as low frequency sounds. According to this approach, the auditory input stimulates movement of the receptors in the middle ear, allowing the cochlear and vestibular systems to facilitate perception of time and space.

Dr. Alfred Tomatis determined that sound may be used to stimulate the vestibular system. In his studies, he used music recorded with specific emphasis on low and mid-range frequencies (e.g., 0-750 Hz) to enhance and support awareness of the body.

Autistic individuals, particularly autistic children, also desire assimilation into social environments, without fear of stigmatization. The sleeping bag is one prominent accessory to many child and adolescent social activities (e.g., camping trips, slumber parties, and day-care or pre-school nap-time sessions). The conventional sleeping bag, however, fails to provide an autistic individual with any therapeutic sensory stimulation to alleviate autism-related anxiety or discomfort.

Accordingly, there is a need in the art for a sleeping bag that provides a user with an appropriate, adjustable level of deep pressure, vibration, and low frequency sound.

SUMMARY OF INVENTION

In view of the unique needs of autistic persons, embodiments of the present invention relate generally to a sleeping bag particularly suited for use by an autistic person as a therapeutic aid. One embodiment of the present invention relates to a sleeping bag having an inflatable interior section, and, more specifically, to a sleeping bag that provides adjustable levels of deep pressure to surround the bag's occupant via one or more inflatable bladders controllably via a pump attachment. Further embodiments of the present invention include a vibratable lining adapted to emit a sound to provide the bag's occupant with additional tactile and auditory stimulation. Thus, embodiments of the present invention include pressure, vibration and sound components. Alternatively, embodiments may include a combination of the pressure and vibration components, or a combination of the pressure component and sound component. Thus embodiments of the present invention include a vibratable, inflatable, sound-emitting sleeping bag; a vibratable, inflatable sleeping bag; and a sound-emitting, inflatable sleeping bag.

The present invention relates generally to a vibratable, sound-emitting, and inflatable sleeping bag that surrounds a user and provides adjustable levels of direct, deep pressure and other tactile and auditory stimulation. Embodiments of the present invention may also include a vibratable, inflatable sleeping bag, or a sound-emitting inflatable sleeping bag. A further embodiment is a sleeping bag that includes an inflatable interior lining comprising one or more bladders adapted to inflate and deflate at the control of the bag's user.

According to an embodiment of the present invention, inflation and deflation of the one or more inflatable bladders is controlled by an inflation system. The inflation system may include a pump and release system manually operable by the user to control the level of deep pressure provided by the inflatable bladders upon the bag's occupant. According to an aspect of the present invention, each inflatable bladder is connected to the pump and release system by a connecting tube that channels the air flowing to and from the bladder. Preferably, the inflation system is controllable by the user using a simple, easy-to-use inflation controller. The user may use a hand-held pump control to adjust the level of pressure provided to his or her body based on the level of inflation of the bladders surrounding the user.

According to another embodiment of the present invention, the inflatable bladders are connected to the inflation system such that the air is distributed to and released from the bladders in a uniform manner. As such, substantially uniform or isostatic pressure may be applied to the user. Advantageously, applying substantially uniform pressure provides the user with the comfort of a deep, surrounding contact without areas of unequal amounts of pressure that may lead to discomfort.

According to yet another embodiment of the present invention, the one or more inflatable bladders may be removed from the sleeping bag's interior lining and/or disconnected from the inflation system to provide the user with a customizable application of direct pressure. This allows the user to select particular bladders to inflate in order to customize the level and direction of pressure provided by the sleeping bag.

Further, according to an aspect of the present invention, the sleeping bag includes an exterior lining that is fixed to and covers the interior lining including the inflatable bladders.

According to another aspect of the present invention, the sleeping bag includes a standard air pump/release system.

According to yet another aspect of the present invention, the inflatable bladders are enclosed and fixedly secured within the interior section of the sleeping bag.

According to an additional embodiment of the present invention, the surface of the interior section making contact with the user is made of a soft, tactile material to optimize comfort. The exterior section of the sleeping bag is made of standard material used in a sleeping bag.

BRIEF DESCRIPTION OF THE DRAWING

The present invention will be more readily understood from the detailed description of the preferred embodiment(s) presented below considered in conjunction with the attached drawing, of which.

DETAILED DESCRIPTION OF THE INVENTION

Figure 1:
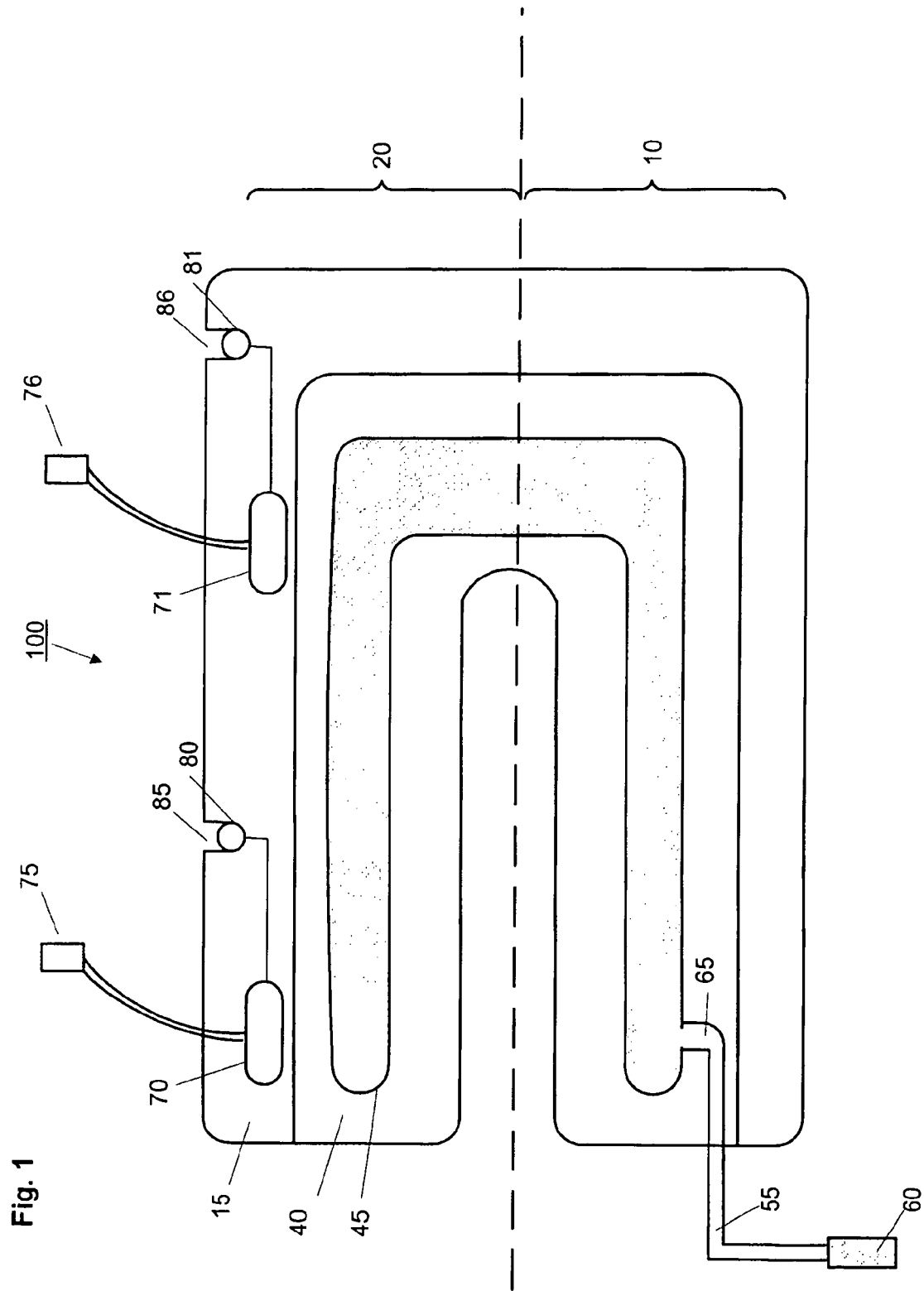
FIG. 1 is a side view of a cross-sectioned sleeping bag, according to an embodiment of the present invention.

Referring to FIG. 1, an embodiment of the present invention is an inflatable sleeping bag 100 that includes a lower portion 10 and an upper portion 20. The lower portion 10 and the upper portion 20 are adapted to join together such that a shell is formed therebetween adapted to enclose an occupant of the sleeping bag 100. According to an embodiment of the present invention, the lower portion 10 is adapted to lie underneath the occupant and the upper portion 20 is adapted to lie on top of the occupant. Preferably, the lower portion 10 and the upper portion 20 are adapted to fasten to one another to form the occupant's enclosure using any standard fastening mechanism (e.g., a zipper, one or more buttons, etc.). According to an embodiment of the present invention, the lower portion 10 and the upper portion 20 include an interior lining 40.

The interior lining 40 includes one or more structures adapted to inflate and deflate, referred to as inflatable bladders 45, connected to an inflation system. One having ordinary skill in the art will appreciate that the interior lining 40 may include a single inflatable bladder 45 spanning all or a portion of the surface of the interior lining 40 or a plurality of inflatable bladders 45 adapted to provide the desired distribution of direct pressure to the occupant. According to an embodiment of the present invention, the one or more inflatable bladders 45 may be inflated such that an even distribution of deep pressure is applied to the bag's occupant.

According to an embodiment of the present invention, the inflation system may include a pump and release mechanism 60 connected to a main tube 55, which is in turn connected to one or more connecting tubes 65. The network of connecting tubes 65 are used to connect each of the inflatable bladders 45 to the pump and release mechanism 60. When air is caused to enter the main tube 55 by the pump and release mechanism 60, the air is passed by the main tube 55 to the one or more connecting tubes 65 and into the one or more inflatable bladders 45. Each inflatable bladder 45 may be adjustably inflated to provide a desired level of deep pressure to the occupant of the sleeping bag. Advantageously, by controlling the pump and release mechanism 60, the occupant may control the amount and location of deep pressure provided, so as to avoid general or local numbness due to excessive pressure or increase the amount of pressure generally or locally to the occupant's liking.

Optionally, the one or more connecting tubes 65 may be individually detached from their corresponding inflatable bladders 45 to allow the user to select which of the one or more inflatable bladders 45 to inflate, thus allowing for the amount and location on the body of the deep pressure to be customized. For example, if a particular user finds that he or she prefers a large amount of deep pressure to be applied to his or her chest area while preferring no direct pressure upon his or her arms, the user may elect to terminate the air flow to the one or more inflatable bladders 45 positioned in the sleeping bag 100 at a location at or near the user's arms.

According to an embodiment of the present invention, disposed within either an exterior lining 15 or the interior lining 40 is a vibrating component 70. According to an embodiment of the present invention, the vibrating component 70 is arranged within the exterior lining 15 of the sleeping bag 100. The vibrating component 70 vibrates to cause at least a portion of the sleeping bag 100 having contact with the bag's occupant to vibrate. The vibrating component 70 may be arranged such that the upper portion 20, the lower portion 10, or both the upper portion 20 and the lower portion 10 of the sleeping bag 100 are caused to vibrate. One having ordinary skill in the art will appreciate that any suitable vibrating mechanism may be employed as the vibrating component 70 of the present invention.

According to an embodiment of the present invention, the vibrating component 70 is adapted to provide an adjustable level of vibration and sound emission. Optionally, the sleeping bag 100 includes a vibration controller 75 communicatively connected to the vibrating component 70 for controlling the level of vibration and/or sound emission provided by the vibrating component 70. One having ordinary skill in the art will appreciate that the vibration controller 75 may be connected to the vibrating component 70 via either a wired connection 72 or a wireless connection (not shown).

According to an embodiment of the present invention, the vibrating component 70 emits a sound having a therapeutic quality. Preferably, the vibrating component 70 provides a low level frequency, having, for example, a hum-like auditory quality. The term "therapeutic quality" as it is used herein refers to, but is not limited to, those sounds which produce a remedial, calming affect on the listener. One having ordinary skill in the art will appreciate that the particular frequency, volume, level, tone, etc., of the sound emitted by the vibrating component 70 is such that it produces a calming effect on a listener, particularly a child, and even more particularly and autistic child.

According to an embodiment of the present invention, disposed within either an exterior lining 15 or the interior lining 40 is a sound-emitting component 71. Preferably, the sound-emitting component 71 provides a low level frequency sound, having, for example, a hum-like auditory quality. According to an embodiment of the present invention, the sound-emitting component 71 is arranged within the exterior lining 15 of the sleeping bag 100. The sound-emitting component 71 produces a sound having a therapeutic affect. One having ordinary skill in the art will appreciate that any suitable sound-emitting mechanism may be employed as the sound-emitting component 71 of the present invention.

According to an embodiment of the present invention, the sound-emitting component 71 provides a low level frequency sound, having, for example, a hum-like auditory quality. One having ordinary skill in the art will appreciate that the particular frequency, volume, level, tone, etc., of the sound emitted by the sound emitting component 71 is such that it produces a calming effect on a listener, particularly a child, and even more particularly and autistic child.

According to an embodiment of the present invention, the sound-emitting component 71 is adapted to provide an adjustable level of sound emission. Optionally, the sleeping bag 100 includes a sound-emitting component controller 76 communicatively connected to the sound-emitting component 71 for controlling the level of vibration and/or sound emission provided by the sound-emitting component 71. One having ordinary skill in the art will appreciate that the sound-emitting controller 76 may be connected to the sound-emitting component 71 via either a wired connection 73 or wireless connection (not shown).

Optionally, the sleeping bag 100 may include a single controller for the user to control the inflation, vibration, and sound emission levels. For example, the vibration controller 75 may serve as a single user interface for control of the inflation, vibration and sound emission levels. Alternatively, the sound emission controller 76 may serve as a single user interface for control of the inflation, vibration and sound emission levels. Preferably, the controllers (i.e., the vibration component controller and the sound-emission component controller) are easy to manipulate and especially designed for use by a child.

The vibrating component 70 may be powered by a standard power supply source 80, such as for example a battery. Optionally, the power supply source 80 may include a jack or outlet 85 accessible from the exterior of the sleeping bag 100 that may be used to recharge the power supply 80 or connect the vibrating mechanism to an external power source, such as, for example, a standard AC power source.

Optionally, the sound-emitting component 71 may be powered by either its own standard supply source 81 or by the power supply source that powers that powers the vibrating component 80. Likewise, the sound-emitting component may include its own jack or outlet 86 or utilize the jack or outlet of the vibrating component 85.

According to an embodiment of the present invention, the interior lining 40 may be opened to allow access to the one or more inflatable bladders 45. The one or more inflatable bladders 45 may be attached within the interior lining 40 in a manner such that the inflatable bladders 45 may be moved or removed. Accordingly, a position of the inflatable bladder 45, and thus the location of the pressure provided thereby, may be changed by detaching the inflatable bladder 45, moving the inflatable bladder 45 to the desired location and reattaching the inflatable bladder 45.

According to an embodiment of the present invention, the connecting 65 tube may be detachable from the one or more inflatable bladders 45 to stop air flow and inflation of that inflatable bladder 45 to allow the user to customize the amount and location of deep pressure provided by the sleeping bag 100.

According to another embodiment of the present invention one or more of the inflatable bladders 45 may be detached, relocated and reattached to the same connecting tube 65 or to a connecting tube 65 at another location in the sleeping bag 100.

According to a further embodiment of the present invention, the one or more inflatable bladders 45 may be removed completely from the sleeping bag 100, without disturbance to the functioning of the inflation system, so as to focus the level of deep pressure on select regions of the body, as desired by the occupant.

One having ordinary skill in the art will appreciate that the interior lining 40 and the exterior lining 15 may be composed of any suitable material conventionally used in a sleeping bag or blanket arrangement. For example, the exterior lining 15 may include a weather-resistant outer surface to allow for use of the sleeping bag in an outdoor environment. Further, in order to facilitate social assimilation, the exterior lining may be embossed with, among other things, images of persons, cartoon characters, or logos popular among children or combinations thereof.

It is to be understood that the above-described embodiments are merely illustrative of the present invention and that many variations of the above-described embodiments can be devised by one skilled in the art without departing from the scope of the invention. It is therefore intended that such variations be included within the scope of the following claims and their equivalents.

What is claimed is:

1. A sleeping bag comprising:
   an interior lining adapted to form an enclosure configured to substantially surround an occupant;
   an exterior lining attached to the interior lining;
   a plurality of inflatable bladders disposed within the interior lining and substantially surrounding the enclosure wherein each of the inflatable bladders is configured to provide adjustable levels of consistent pressure selectively directable to the occupant of the sleeping bag;
   an inflation system for individually inflating and deflating at least one of the plurality of inflatable bladders; and
   a vibrating component configured to vibrate at least a portion of the interior lining and emit a sound.

2. The sleeping bag of claim 1, wherein each of the inflatable bladders are configured to provide an adjustable level of consistent deep pressure selectively directable to the occupant of the sleeping bag.

3. The sleeping bag of claim 1, wherein the inflation system comprises a pump and release mechanism connected to a main tube, and one or more connecting tubes connected to the main tube and to at least one of the plurality of inflatable bladders.

4. The sleeping bag of claim 3, wherein each of the one or more connecting tubes are detachable from at least one of the plurality of inflatable bladders.

5. The sleeping bag of claim 3, wherein at least one of the plurality of inflatable bladders may be detached from a connecting tube at one location and reattached to a connecting tube at another location.

6. The sleeping bag of claim 1, wherein vibrating component emits an adjustable sound.

7. The sleeping bag of claim 6, wherein the adjustable sound has a therapeutic quality.

8. The sleeping bag of claim 6, wherein the adjustable sound has a frequency of less than or equal to 750 Hz.

9. The sleeping bag of claim 6, further comprising a single controller for controlling inflation, vibration and sound emission levels.

10. The sleeping bag of claim 1, further comprising a vibration controller connected to the vibrating component for adjusting the level of vibration.

11. The sleeping bag of claim 1, further comprising a sound-emitting component.

12. The sleeping bag of claim 11, wherein the sound-emitting component is adapted to emit an adjustable level of sound emission.

13. The sleeping bag of claim 11, further comprising a sound-emitting controller connected to the sound-emitting component for controlling the level of sound emission provided by the sound-emitting component.

* * * * *